United States Patent [19]

Regan et al.

[11] Patent Number: 5,132,312

[45] Date of Patent: Jul. 21, 1992

[54] SUBSTITUTED CYCLOHEXENE DERIVATIVES AS HMG-COA REDUCTASE INHIBITORS

[75] Inventors: John R. Regan, Princeton, N.J.; Kent E. Neuenschwander, Ambler, Pa.

[73] Assignee: Rhone-Poulenc Rorer Pharmaiceuticals Inc., Collegeville, Pa.

[21] Appl. No.: 618,754

[22] Filed: Nov. 27, 1990

Related U.S. Application Data

[63] Continuation-in-part of Ser. No. 510,351, Apr. 17, 1990, Pat. No. 5,001,144, which is a continuation-in-part of Ser. No. 412,356, Sep. 25, 1989, Pat. No. 4,939,143, which is a continuation-in-part of Ser. No. 328,836, Mar. 27, 1989, Pat. No. 4,900,754.

[51] Int. Cl.$^5$ .............. A61K 31/17; A61K 31/365; C07D 215/16; C07D 309/10

[52] U.S. Cl. .................. 514/312; 549/292; 558/270; 558/271; 558/272; 560/9; 560/12; 560/13; 560/14; 560/27; 560/39; 560/31; 560/32; 562/429; 562/430; 562/431; 562/441; 562/469; 546/268; 546/296; 546/297; 546/298; 546/301; 546/302; 546/300; 546/307; 546/309; 546/153; 546/155; 546/159; 546/162; 514/478; 514/512; 514/532; 514/533; 514/542; 514/559; 514/570; 514/562; 514/563; 514/459; 514/460; 514/414; 514/418; 514/824; 514/313; 514/336; 514/352; 514/318; 514/341; 514/351; 514/315; 548/467; 548/472; 548/475

[58] Field of Search .......... 560/12, 13, 14, 39, 560/27, 54, 56, 9, 31, 32; 562/429, 430, 431, 441, 469; 549/292; 546/268, 298, 296, 297, 301, 302, 300, 307, 309, 153, 155, 159, 162; 548/467, 472, 475; 514/478, 512, 532, 533, 535, 538, 542, 559, 570, 562, 563, 459, 460, 414, 418, 824, 336, 313, 312, 352, 348, 349, 351, 345; 558/270, 271, 272

[56] References Cited

U.S. PATENT DOCUMENTS

| | | | |
|---|---|---|---|
| 4,282,155 | 8/1981 | Smith et al. | 549/292 |
| 4,308,378 | 12/1981 | Stokker | 549/292 |
| 4,503,072 | 3/1985 | Hoffman et al. | 514/459 |
| 4,567,289 | 1/1986 | Willard et al. | 560/59 |
| 4,611,067 | 9/1986 | Volante et al. | 556/416 |
| 4,622,338 | 11/1986 | Baran et al. | 549/292 |
| 4,668,699 | 5/1987 | Hoffman et al. | 560/119 |
| 4,681,893 | 7/1987 | Roth | 514/423 |
| 4,772,629 | 9/1988 | Smith et al. | 549/292 |

Primary Examiner—Richard L. Raymond
Assistant Examiner—Mark W. Russell
Attorney, Agent, or Firm—Raymond S. Parker, III; Martin F. Savitzky

[57] ABSTRACT

Disclosed are novel 3-hydroxy-3-methylglutarylcoenzyme A reductase inhibitors useful as antihypercholesterolemic agents represented by the formula

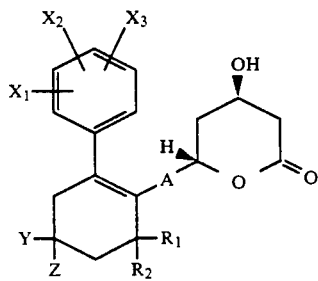

and the corresponding ring-opened hydroxy acids derived therefrom and pharmaceutically acceptable salts thereof.

Pharmaceutical compositions containing said compounds and method of inhibiting the biosynthesis of cholesterol therewith are also disclosed.

20 Claims, No Drawings

SUBSTITUTED CYCLOHEXENE DERIVATIVES AS HMG-COA REDUCTASE INHIBITORS

BACKGROUND OF THE INVENTION

This application is a continuation-in-part application of United States Patent Application Ser. No. 07/510,351 filed Apr. 17, 1990, now U.S. Pat. No. 5,001,144 issued Mar. 19, 1991 which, in turn is a continuation-in-part of United States Application Ser. No. 07/412,356 filed Sept. 25, 1989 now U.S. Pat. No. 4,939,143 issued Aug. 3, 1990, which, in turn, is a continuation-in-part application of United States Application Ser. No. 07/328,836 filed Mar. 27, 1989 U.S. Pat. No. 4,900,754 issued Feb. 13, 1990.

1. Field of the Invention

The present invention relates to compounds, pharmaceutical compositions and a method useful for reducing serum cholesterol in humans. More particularly, the invention relates to substituted cyclohexene derivatives, the corresponding ring opened hydroxy acids derived therefrom and pharmaceutically acceptable salts thereof which are potent inhibitors of the enzyme 3-hydroxy-3-methyl-glutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Related Prior Art

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]- 4-hydroxypyran-2-ones useful as hypocholesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,567,289 relates to ,methyl, ethyl, n-propyl, 2-(acetylamino)ethyl, or 1-(2,3-dihydroxy)propyl ester of E-(3R,5S)-7-(4'-fluoro-3,3',5-trimethyl[1,1'-biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

European Patent Application No. 87,305,527.1 (Publication No. 0,251,625) discloses HMG-CoA reductase inhibitors having the structures I and II.

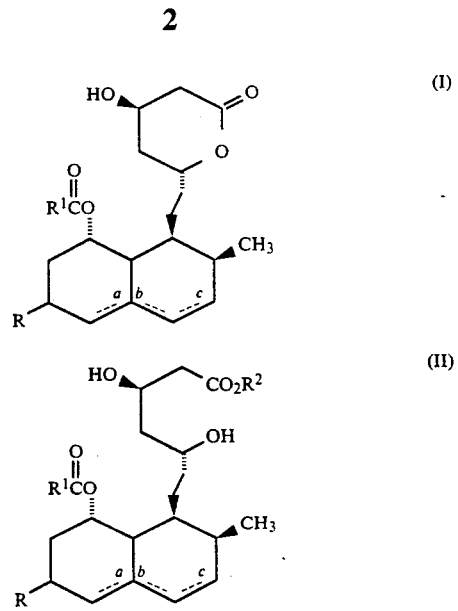

SUMMARY OF THE INVENTION

In accordance with the present invention, certain substituted cyclohexene derivatives, the corresponding ring opened hydroxy acids derived therefrom and pharmaceutically acceptable salts thereof are provided which are potent inhibitors of HMG-CoA reductase. Specifically, the invention provides compounds of formula I.

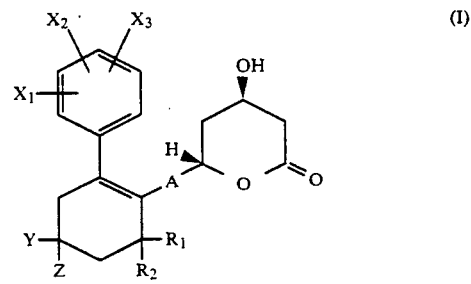

wherein:

(a) In one embodiment of the invention:
  A is $CH_2-CH_2$, $CH=CH$ or $-C\equiv C-$;
  $X_1$, $X_2$ and $X_3$ are independently: H, $C_{1-6}$ alkyl, halogen, $RO(CH_2)_m-$, aryl, $NR_1R_2$ or $SO_mR_1$;
  Y is azetidyl, pyrrolidyl, pyrrolyl, piperidyl, pyridyl, succinimido or phthalimido;
  R, $R_1$, $R_2$ and Z are independently: H or $C_{1-6}$ alkyl;
  m is 0, 1 or 2; its hydroxy acids and the pharmaceutically acceptable salts thereof.

Examples of this embodiment are the following compounds:

1. trans-(E)-6-{2-{2-(4-fluoro-3-methylphenyl)-4-(pyrrolidin-1-yl)-6,6-dimethylcyclohex-1-en-1-yl}ethenyl}-4-1 hydroxy-3,4,5,6-tetrahydro-2H-pyran-2-one;

2. trans-(E)-6-{2-{2-(4-fluoro-3-methylphenyl)-4-succinimido-6,6-dimethylcylcohex-1-en-1-yl}ethenyl}-4-hydroxy-3,4,5,6-tetrahydro-2H-pyran-2-one;

3. trans-(E)-6-(2-(2-(4-fluoro-3-methylphenyl)-4-phthalimido-6,6-dimethylcylcohex-1-en-1-yl}ethenyl}-4-hydroxy-3,4,5,6-tetrahydro-2H-pyran-2-one;

4. trans-6-{2-(2-(4-fluorophenyl)-4-(pyridin-4-yl)-6,6-dimethylcylcohex-1-en-1-yl}ethyl}-4-hydroxy-3,4,5,6-tetrahydro-2H-pyran-2-one; and
5. trans-6-{2-{2-(4-fluoro-3-hydroxymethyl)-4-(piperdin-1-yl)-6,6-dimethylcylcohex-1-en-1-yl}ethyl-}-4-hydroxy-3,4,5,6-tetrahydro-2H-pyran-2-one.

(b) In the second embodiment of the invention of formula I:
A is $CH_2CH_2$, $CH=CH$ or $C\equiv C$;
$X_1$, $X_2$ and $X_3$ are independently: H, $C_{1-6}$ alkyl, halogen, $RO(CH_2)_m$—, aryl, $NR_1R_2$ or $SO_mR_1$;
Z is a chemical bond;
Y is —$O(CR_1R_2)_nO$— or —$S(CR_1R_2)_nS$— and Z and Y are joined together and form a heterocyclic ring with the carbon atom of the cyclohexene ring;
R, $R_1$ and $R_2$ are independently: H or $C_{1-6}$ alkyl;
n is 2, 3 or 4;
m is 0, 1 or 2; its hydroxy acids and pharmaceutically acceptable salts thereof.

Examples of this embodiment are the following compounds:
1. trans-(E)-6-(2-{7-(4-fluorophenyl)-9,9-dimethyl-1,4-dioxaspiro[4.5]dec-7-en-8-yl}ethenyl}-4-hydroxy-3,4,5,6-tetrahydro-2H-pyran-2-one;
2. trans-(E)-6-{2-(8-(4-fluorophenyl)-10,10-dimethyl-1,5dithiaspiro{5.5}undec-8-en-9-yl}ethenyl}-4-hydroxy3,4,5,6-tetrahydro-2H-pyran-2-one;
3. trans-6-{2-{8-(4-fluoro-3-methylphenyl)-10,10-dimethyl-1,5-dithiaspiro(5.5)undec-8-en-9-yl}ethyl}-4-hydroxy-3,4,5,6-tetrahydro-2H-pyran-2-one;
4. trans-(E)-6-{2-{8-(4-fluoro-3-hydroxymethyl)-10,10-dimethyl-1,5-dithiaspiro{5.5}undec-8-en-9-yl}ethenyl}-hydroxy-3,4,5,6-tetrahydro-2H-pyran-2-one; and
5. trans-6-{2-{8-(4-chloro-3-fluorophenyl)-10,10-dimethyl-1,5-dithiaspiro{5.5}undec-8-en-9-yl}ethyl-4-hydroxy-3,4,5,6-tetrahydro-2H-pyran-2-one.

(c) In the third embodiment of the invention of formula I:
A is $CH_2CH_2$, $CH=CH$, or $C\equiv C$;
$X_1$, $X_2$ and $X_3$ are independently: H, $C_{1-6}$ alkyl, halogen, $RO(CH_2)_m$—; aryl, $NR_1R_2$ or $SO_mR_1$;
R, $R_1$, $R_2$ and Z are independently: H or $C_{1-6}$ alkyl;
Y is

Q is $NR_3R_4$ or $OR_3$;
$R_3$ and $R_4$ are independently: H, $C_{1-6}$ alkyl, aryl, substituted aryl, heteroaryl or substituted heteroaryl;
m is 0,1 or 2; its hydroxy acids and pharmaceutically acceptable salts thereof.

Examples of this embodiement are the following compounds:
1. trans-(E)-6-{2-{2-(4-fluoro-3-methylphenyl)-4-phenylcarbamoyloxy-6,6-dimethylcyclohex-1-en-1-yl}ethenyl}-4-hydroxy-3,4,5,6-tetrahydro-2H-pyran-2-one;
2. trans-(E)-6-{2-{2-(4-fluoro-3-hydroxymethyl)-4-(4-fluorophenylcarbamoyloxy)-6,6-dimethylcyclohex-1-en-1-yl}ethenyl}-4-hydroxy-3,4,5,6-tetrahydro-2H-pyran-2one;
3. trans-6-{2-{2-(4-fluorophenyl)-4-(N-phenyl-N-methylcarbamoyloxy)-6,6-dimethylcyclohex-1-en-1-yl}ethyl}-4-hydroxy-3,4,5,6-tetrahydro-2H-pyran-2-one;
4. trans-(E)-6-{2-{2-(4-chlorophenyl)-4-(3-pyridylcarbamoyloxy)-6,6-dimethylcyclohex-1-en-1-yl}ethenyl}4-hydroxy-3,4,5,6-tetrahydro-2H-pyran-2-one;
5. trans-(E)-6-{2-{2-(4-fluorophenyl)-4-ethylcarbonyldioxy)-6,6-dimethylcyclohex-1-en-1-yl}ethyl}-4-hydroxy-3,4,5,6-tetrahydro-2H-pyran-2-one; and
6. trans-(E)-6-{2-{2-(4-chloro-3-methylphenyl)-4-(4-chloro-3-methylphenylcarbonyldioxy)-6,6-dimethylcyclohex-1-en-1-yl}ethenyl}-4-hydroxy-3,4,5',6-tetrahydro-2H-pyran-2-one.

(d) In the fourth embodiment of the invention of formula I:
A is $CHzCH_2$, $CH=CH$, or $C\equiv C$;
$X_1$, $X_2$ and $X_3$ are independently: H, $C_{1-6}$ alkyl, halogen, $RO(CH_2)_m$—, aryl, $NR_1R_2$ or $SO_mR_1$;
R, $R_1$, $R_2$ and Z are independently: H or $C_{1-6}$ alkyl;
Y is —$O(CR_1R_2)_nC(O)Q$;
Q is $NR_3R_4$ or $OR_3$;
$R_3$ and $R_4$ are independently: H, $C_{1-6}$ alkyl, aryl, substituted aryl or heteroaryl;
n is 1,;2 or 3;
m is 0, 1 or 2; its hydroxy acids and pharmaceutically acceptable salts thereof.

Examples of this embodiment are the following compounds:
1. trans-6-(2-{2-(4-fluoro-3-methylphenyl)-4-ethoxycarbonylmethoxy)-6,6-dimethylcyclohex-1-en-1-yl}ethyl}-4-hydroxy-3,4,5,6-tetrahydro-2H-pyran-2-one;
2. trans-(E)-6-{2-{2-(4-fluorophenyl)-4-(2-(ethoxy-carbonyl)ethoxy)-6,6-dimethylcyclohex-1-en-1-yl}ethenyl}-4-hydroxy-3,4,5,6-tetrahydro-2H-pyran-2one;
3. trans-(E)-6-{2-{2-(4-fluoro-3-ethylphenyl)-4-(2-(4-fluoroanilinocarbonyl)ethoxy)-6,6-dimethylcyclohex-1-en-1-yl}ethenyl}-4-hydroxy-3,4,5,6-tetrahydro-2H-pyran-2-one;
4. trans-(E)-6-{{2-(4-chlorophenyl)-4-(dimethylaminocarbonylmethoxy)-6,6-dimethylcyclohex-1-en-1-yl}ethynyl}-4-hydroxy-3,4,5,6-tetrahydro-2H-pyran-2-one; and
5. trans-(E)-6-(2-(2-(4-fluoro-3-methylphenyl)-4-(4-methoxyanilinocarbonylmethoxy)-6,6-dimethylcyclohex-1-en-1-yl}ethyl}-4-hydroxy-3,4,5,6-tetrahydro-2H-pyran-2-one.

DETAILED DESCRIPTION OF THE INVENTION

Unless expressly indicated otherwise herein, alkyl represents straight-chain or branched chain alkyl; aryl preferably denotes phenyl or naphthyl; substituted aryl means aryl substitution with hydrogen, $C_{1-6}$ alkyl, halogen, $RO(CH_2)_m$, $NR_1R_2$ or $SO_mR_1$ wherein R, $R_1$, $R_2$ and m are as previously defined; preferred heteroaryl are pyridyl, indolyl and quinolyl; substituted heteroaryl means heteroaryl substituted with hydrogen, $C_{1-6}$ alkyl, halogen, $RO(CH_2)_m$, $NR_1R_2$ or $SO_mR_1$ wherein R, $R_1$, $R_2$ and m are as previously defined; halogen denotes Cl, F, Br and I; and alkoxy means $C_{1-6}$ alkoxy.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formulas.

The procedures for producing the compounds of the present invention are as indicated in Schemes I through IX which follow.
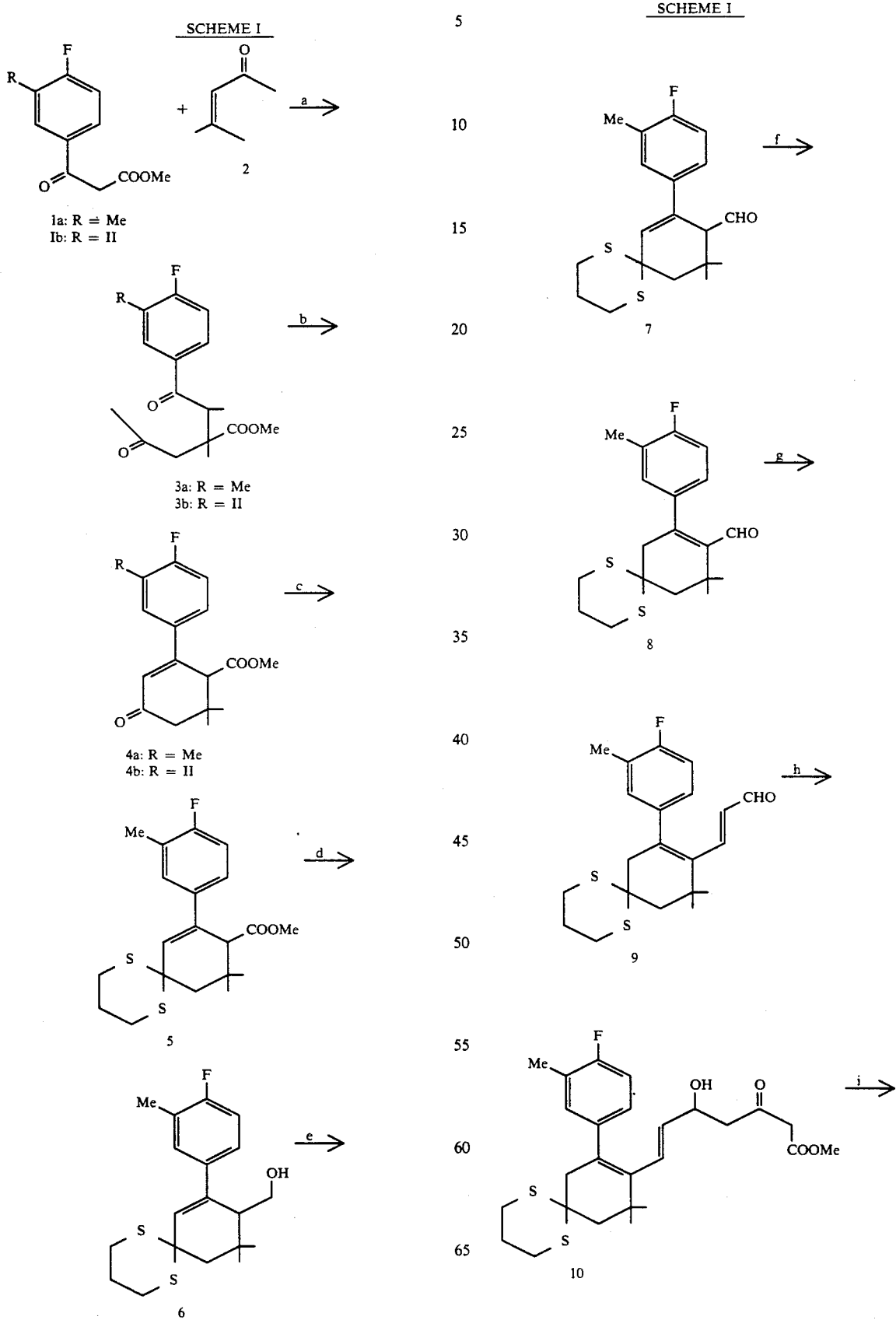

-continued
SCHEME I
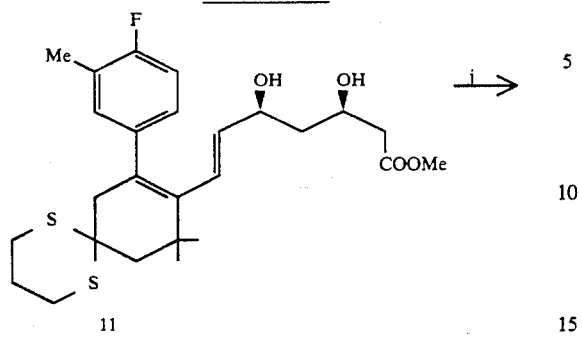
11
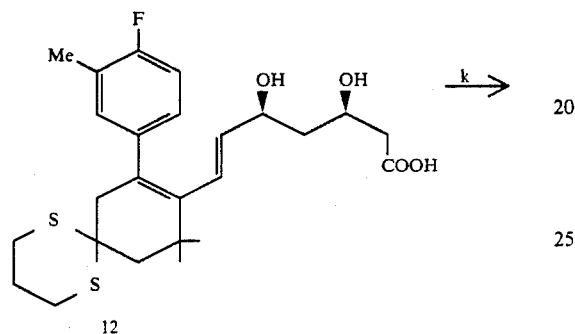
12
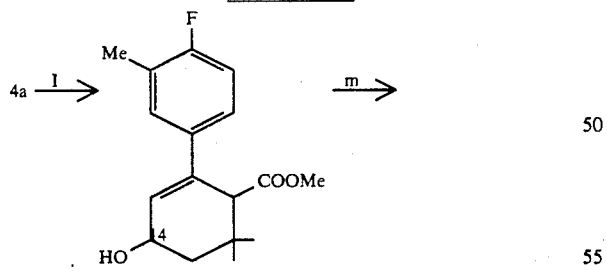
13
SCHEME II
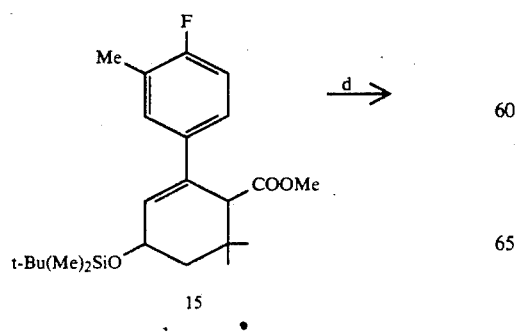
15
-continued
SCHEME II
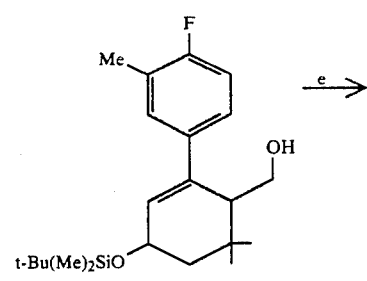
16
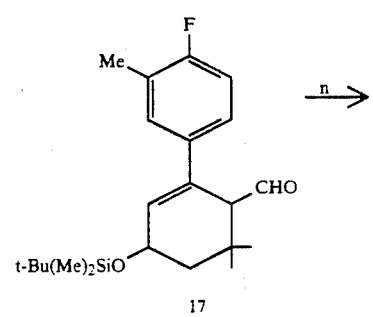
17
18
19
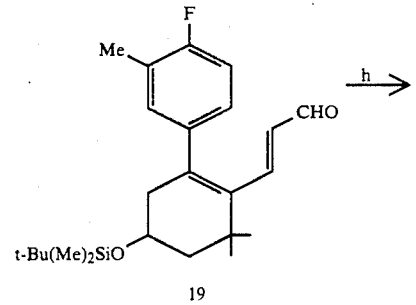
20

-continued
SCHEME II
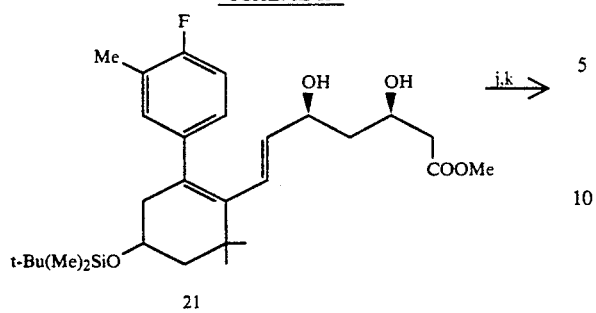
21
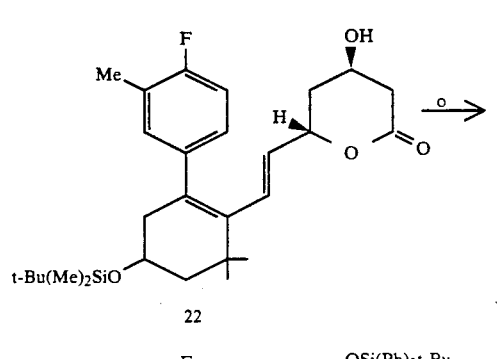
22
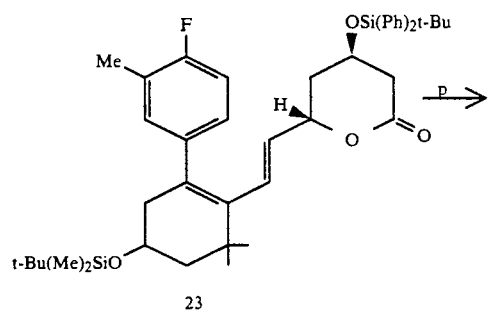
23
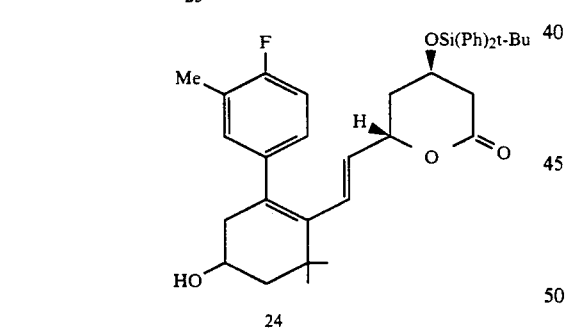
24
SCHEME III
4b →(q)→
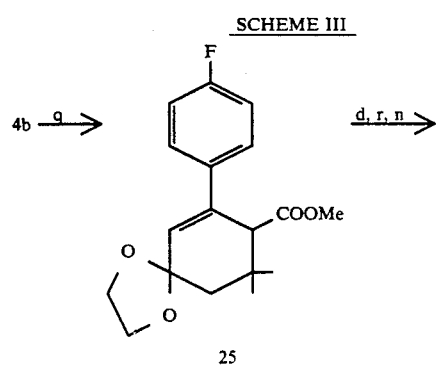
25
-continued
SCHEME III
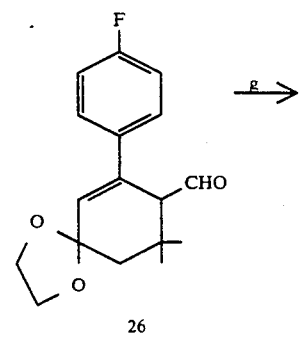
26
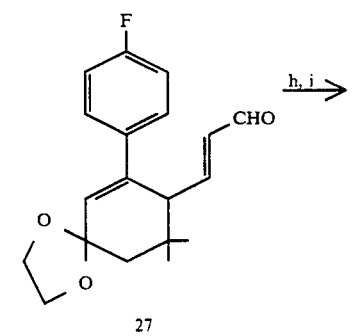
27
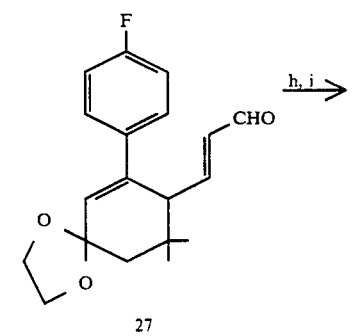
28
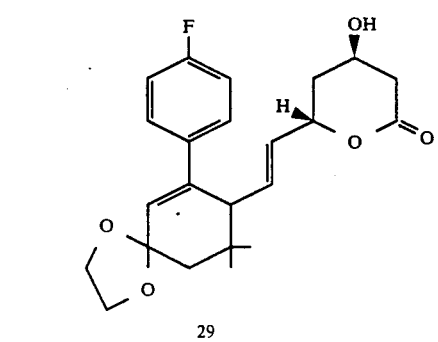
29

SCHEME IV
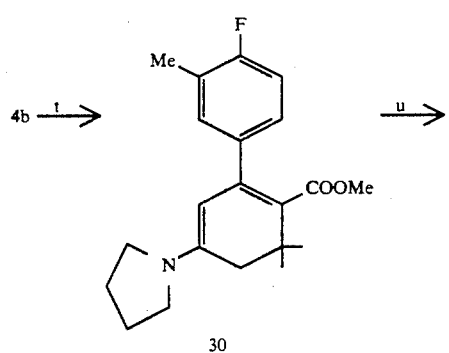
30
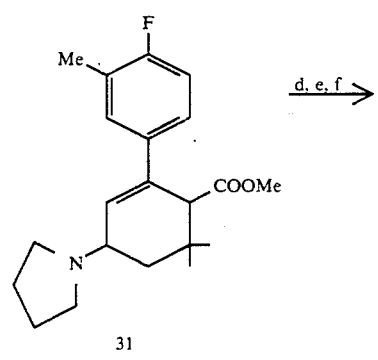
31
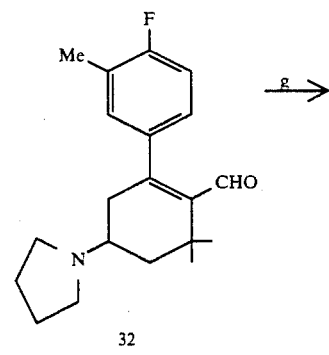
32
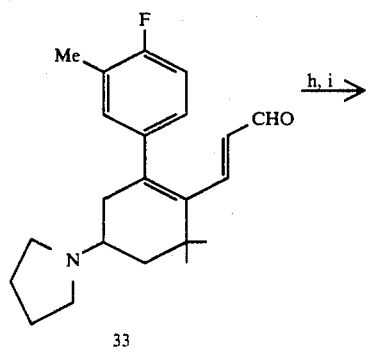
33
-continued
SCHEME IV
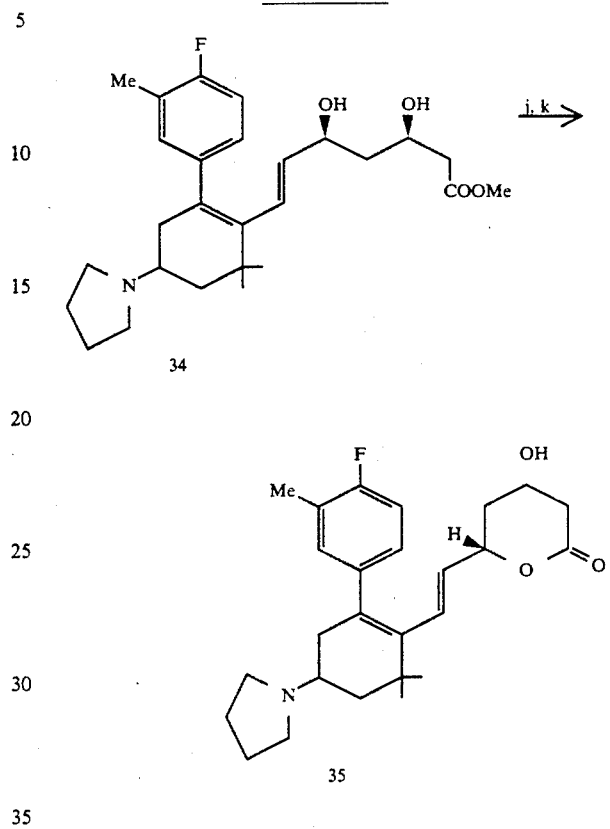
34
35
SCHEME V
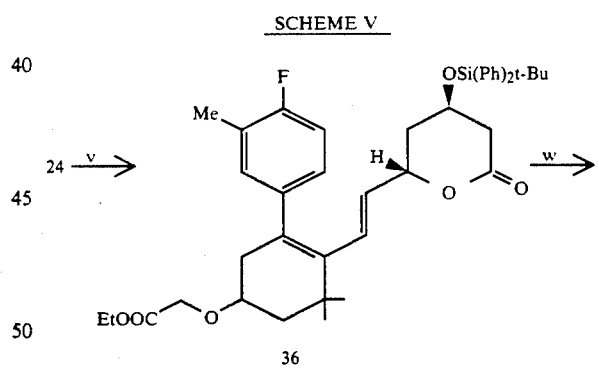
36
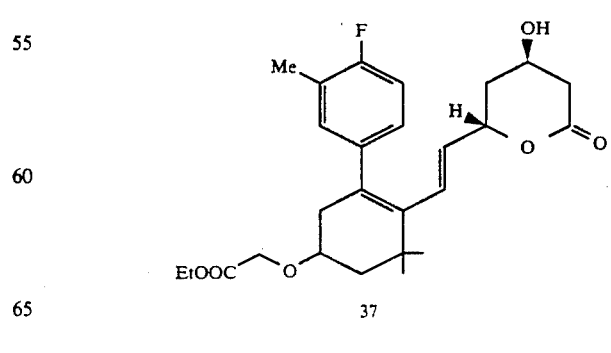
37

SCHEME VI
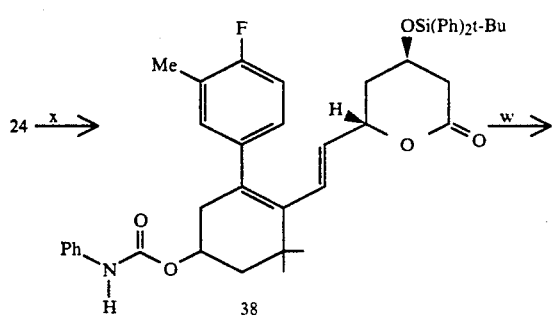
SCHEME VII
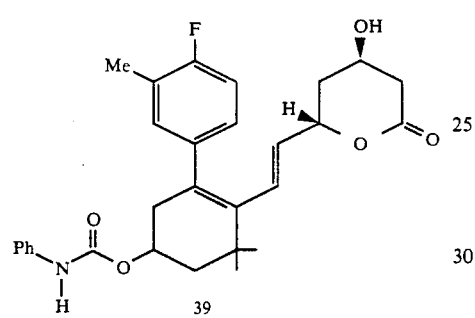
SCHEME VIII
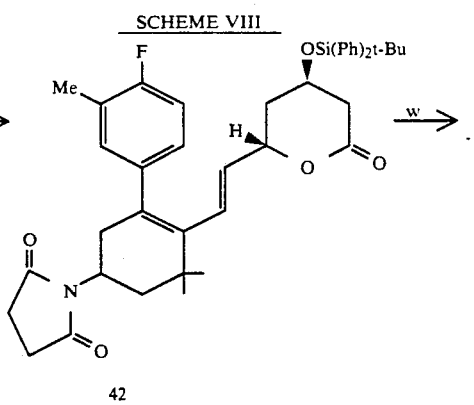
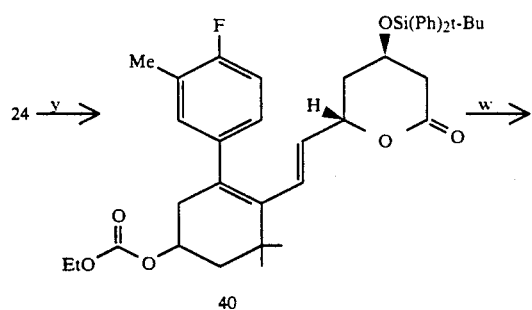
SCHEME IX
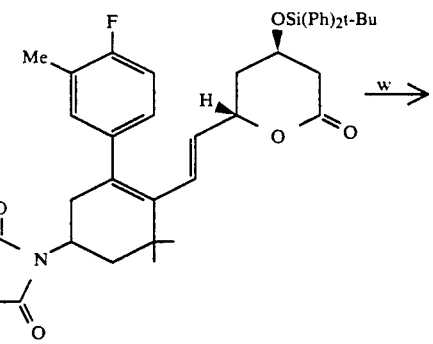
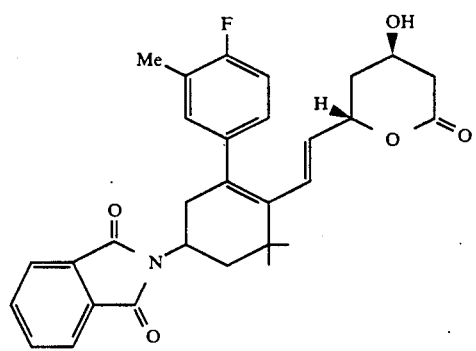

-continued
SCHEME IX

LEGEND
a. BF$_3$ — etherate/0° C.
b. Triton B/MeOH/reflux
c. HSCH$_2$CH$_2$SH/BF$_3$ — Etherate
d. LAH/Ether/0° C.
e. SO$_3$ — Pyridine/DMSO
f. Triton B/MeOH/0° C.
g. (i) C$_6$H$_{11}$N=CHCH$_3$/LDA
   (ii) SiO$_2$
h. CH$_3$COCH$_2$CO$_2$CH$_3$/LDA
i. Et$_3$B/NaBH$_4$/THF/−78° C.
j. NaOH/MeOH
k. ClCO$_2$Et/Et$_3$N/THF/0° C.
l. NaBH$_4$/MeOH
m. Cl(t-Bu)Me$_2$Si/imidazole/CH$_2$Cl$_2$
n. Potassium t-butoxide/THF
o. Cl(t-Bu)Ph$_2$Si/imidazole/CH$_2$Cl$_2$
p. HOAc/H$_2$O/THF/3:1:1
q. HOCH$_2$CH$_2$OH/toluene/PPTS/reflux
r. PCC/CH$_2$Cl$_2$
s. DCC/DMAP/ether
t. Pyrrolidine/HCl/MeOH
u. NaCNBH$_3$/MeOH
v. N$_2$CHOOEt/Rh$_2$(OAc)$_4$/CH$_2$Cl$_2$
w. (n-Bu)$_4$NF/THF/HOAc
x. PhNCO/DMF
y. ClCOOEt/pyridine/CH$_2$Cl$_2$
z. Succinimide/Ph$_3$P/EtOOCN=NCOOEt/THF
aa. Phthalimide/Ph$_3$O/EtOOCN=NCOOEt/THF The starting materials were obtained from the Aldrich Chemical Co. but they may also be synthesized in accordance with methods known in the art.

The following preparative examples will further illustrate the invention. In the examples, the underlined parenthetical numbers from 1 through 45 refer to and identify the structures shown in Schemes I through IX.

EXAMPLE 1 (Scheme I)

A. Methyl 3.3-dimethyl-2-(4-fluoro-3-methylbenzoyl)-5-oxohexanoate (3a)

A mixture of methyl 4-fluoro-3-methylbenzoylacetate (1a) (26.95g, 0.128 mol) and mesityl oxide (2) (19.3g, 0.192 mol) was kept at 0°–5° C. for 5 days, poured onto cold saturated NaHCO$_3$ and extracted with ether. The combined extracts were washed with H$_2$O and brine and dried (MgSO$_4$). Removal of the volatiles in vacuo furnished 3a which was used without further purification.

B. Methyl 2.2-dimethyl-6-(4-fluoro-3-methylohenyl)-cyclohex-5-en-1-carboxylate (4a)

A solution of 3a and Triton B (25 mL of 40% in methanol) in 200 mL anhydrous methanol was heated at reflux for 1 hour, cooled, acidified with aqueous HCl and extracted with ether. The combined extracts were washed with H$_2$O and brine and dried (MgSO$_4$). Removal of volatiles in vacuo and purification of the residue by HPLC using 8:1 hexanes: EtOAc as eluents provided 22.5 gm of the solid product.

C. Methyl 8-(4-fluoro-3-methylohenyl)-10,10-dimethyl-1.5-dithiaspiro{5.5)undec-7-en-9-carboxvlate (5)

To a solution of 4a (7.75 g, 26.7 mmol) and 1,3-propanedithiol (3.03g, 28.1 mmol) in 50 mL acetic acid was added boron trifluoride etherate (7.98g, 56.2 mmol). The solution was stirred overnight, diluted with ether, washed with H$_2$O, saturated NaHCO$_3$, and brine and dried (MgSO$_4$). Removal of the volatile in vacuo provided a residue which was crystallized from hexane, wt 8.0 g, mp 100°–01° C. Anal. C$_{20}$H$_{25}$FO$_2$S$_2$: Theory C: 63.12; H:6.62; S:16.85. Found C: 63.45; H:6.58; S: 16.44.

D. 8-(4-Fluoro-3-methylphenyl)-9-hvdroxvmethyl-10,10-dimethyl-1,5-dithiasoiro5.5)undec-7-ene(6)

To a solution of 5 (7.77 g, 20.4 mmol) in 80 mL of anhydrous THF at 0°–5° C was added portionwise LAH (0.97 g, 25.6 mmol). The mixture was stirred for 1.5 h, quenched with 1 mL of H$_2$O, 1 mL of 15% NaOH and 3 mL of H$_2$O and filtered. The volatiles were removed in vacuo and the residue recrystallized with hexanes:EtOAc. Wt. 5.55 g. mp 128°–9° C. Anal. C$_{19}$H$_{25}$FOS$_2$; Theory C: 64.74; H: 7.15; S:18.19. Found C: 64.57; H: 7.03; S: 17.71.

E. 8-(4-Fluoro-3-methylphenyl-10,10-dimethyl-1,5-dithiaspiro(5.5)undec-7-en-9-carboxaldehvde (7)

To a solution of 6 (5.6 g, 16.6 mmol) and triethylamine (15 mL, 107 mmol) in 50 mL anhydrous DMSO was added sulfur trioxide pyridine complex (8.1 g, 49.7 mmol). The mixture was stirred for 1 h, at ambient temperature and under a N$_2$ atmosphere, diluted with ether, washed thoroughly with H$_2$O and brine and dried (MgSO$_4$). Removal of the volatiles in vacuo provided a residue which was purified by HPLC using 17:1 hexanes:EtOAc as eluents. Concentration in vacuo of the product-rich fractions furnished 3.90 gm of product.

F. 8-(4-Fluoro-3-methylphenyl)-10,10-dimethyl-1,5-dithiaspiro(5.5)undec-8-en-9-carboxaldehvde (8)

To a solution of (3.90 g, 11.1 mmol) in 30 mL anhydrous methanol at 0°–5° C was added dropwise Triton B (0.23 g, 0.55 mmol, 40% in methanol). The mixture was kept at 0°–5° C overnight, diluted with acetic acid (2 mL), ether and H$_2$O . The organic layer was washed with H$_2$O and brine and dried (MgSO$_4$). Removal of the volatiles in vacuo provided a residue which was purified by HPLC using 40:1 hexanes:EtOAc as the eluents. Concentration in vacuo of the product-rich fractions gave 3.50 gm of the solid product.

G. (E)-3-{8-(4-fluoro-3-methylohenyl)-10,10-dimethyl-1,5-dithiaspiro(5.5)undec-8-en-9-vl)orooenal (9)

To a −20° C. solution of LDA (19.0 mmol) in 60 mL anhydrous THF was added ethylidenecyclohexylamine (Org. Syn. 50, 66) (2.38 gm, 19.0 mmol). The solution was stirred for 30 min, cooled to −78° C. and a solution of 8 (3.50 g, 10.0 mmol) in 60 mL was added. The mixture was stirred for 3 h, diluted with ether and quenched with H$_2$O . The organic layer was washed with H$_2$O and brine and dried (MgSO$_4$). Removal of the volatiles in vacuo and purification of the residue by HPLC using 10:1 hexanes:EtOAc provided 1.6 g of the orange color gum.

H. Methyl (E)-7-{8-(4-fluoro-3-methylphenyl)-10,10-dimethyl-1,5-dithiasoiro{5,5)undec-8-en-9-yl)-5-hvdroxv-3-oxohept-6-enoate (10)

To a −60° C. solution of LDA (15.0 mmol) in 15 mL anhydrous THF was added dropwise methyl acetoncetate (0.592 g, 5.1 mmol). The solution was warmed to 0° C., stirred for 1 h and a solution of 9 (1.6 g, 4.25 mmol) in 15 mL anhydrous THF was added. The mixture was stirred for 1 h, and quenched with acetic acid (1 mL), $H_2O$ and ether. The organic layer was washed with $H_2O$, saturated $NaHCO_3$ and brine and dried ($MgSO_4$) Removal of the volatiles in vacuo and purification of the residue by HPLC using 3:1 hexanes:EtOAc as elevents furnished 1.4 g of rust colored oil.

I. Methyl (E)-7-(8-(4-Fluoro-3-methylphenyl)-10,10-dimethyl-1,5-dithiaspiro(5.5)undec-8-en-9-yl)-3,5-dihydroxy-hept-6-enoate (11)

To a solution of 10 (1.4 g, 2.84 mmol) and triethyl borane (4.3 mL, 4.26 mmol) in 12 mL anhydrous THF which was stirred at ambient temperature for 5 min., cooled to −78° C. and $NaBH_4$ (0.125 g, 3.27 mmol) was added followed by the slow dropwise addition of anhydrous methanol (2mL). The mixture was stirred for 45 min., quenched with aqueous $H_2O_2$ (1.9 mL of a 6:13 mixture Of 30% $H_2O_2$–$H_2O$ mixture), warmed to ambient temperature over 1 h and diluted with EtOAc and aqueous HCl. The organic layer was washed with $H_2O$, and brine and dried ($MgSO_4$) Removal of the volatiles and purification of the residue by HPLC using 2:1 hexanes:EtOAc as eluents yielded 1.1 g of tan colored gum.

J. (E)-3,5-dihydroxy-7-{8-(4-fluoro-3-methylphenyl)-10,10-dimethyl-1,5-dithiaspiro(5,5}undec-8-en-9-yl}hept-6-enoic acid (12)

To a solution of 11 (1.05 g, 2.12 mmol) in 10 mL of methanol at 0°–5° C. was added dropwise aqueous NaOH (2.1 mL of 1N, 2.1 mmol). The mixture was stirred for 1 h and most of the volatiles were removed in vacuo. The residue was acidified with aqueous HCl to pH 3 and extracted with ether. The combined extracts were washed with brine and dried ($MgSO_4$). Removal of the volatiles in vacuo gave 0.90 gm of tan colored solid.

K. Trans-(E)-6-(2-(8-(4-fluoro-3-methylphenyl)-10,10-dimethyl-1,5-dithiaspiro(5,5)undec-8-en-9-yl)ethenyl)-4-hydroxy-3,4,5,6-tetrahydro-2H-pyran-2-one (13)

To a 0°–5° C. solution of 12 (0.90 gm, 1.87 mmol) and triethylamine (315 μL, 2.25 mmol) in 10 mL $CH_2Cl_2$ was added dropwise ethyl chloroformate (185 μL, 1.87 mmol). The mixture was stirred for 30 min, diluted with ether, washed with $H_2O$, saturated $NaHCO_3$ and brine and dried ($MgSO_4$). Removal of the volatiles in vacuo and purification of the residue by $SiO_2$ using 3:2 hexanes:EtOAc as eluent provided 0.61 g of the product. mp 136°–8° C. Anal. $C_{23}H_{31}FO_3S_2$: Theory C: 64.91; H: 6.75. Found C: 65.31; H: 6.82.

EXAMPLE 2 (Scheme II)

A. Methyl 2-(4-fluoro-3-methylphenyl)-4-hydroxy-6,6-dimethylcyclohex-2-en-1-carboxylate (14)

To a solution of 4a (13.7 g, 47.2 mmol) in 100 mL of methanol at 0°–5° C. was added $NaBH_4$ (2.68 g, 70.9 mmol). The mixture was stirred for 1 hr, diluted with ether and $H_2O$. The organic layer was washed with $H_2O$ and brine and dried ($MgSO_4$). Removal of the volatiles in vacuo provided a quantitive yield of product which was taken forward without further purification.

B. Methyl 2-(4-fluoro-3-methylphenyl)-4-t-butyldimethylsilyloxy)-6.6-dimethylcyclohex-2-en-l-carboxylate (15)

To a solution of imidazole (9.75 g, 0.142 mmol) in 100 H mL $CH_2Cl_2$ was added dropwise a solution of t-butyl-chlorodimethylsilane (11.0 g, 70.8 mmol) in 50 mL $CH_2Cl_2$. The mixture was stirred for 15 min., a solution of 14 (47.2 mmol) in 100 mL of $CH_2Cl_2$ was added, stirred for overnight and diluted with ether and $H_2O$. The organic layer was washed with $H_2O$ and brine and dried ($MgSO_4$). Removal of the volatiles in vacuo provided a quantitative yield of 15 which was taken forward without further purification.

C. 1-(4-Fluoro-3-methylphenyl)-3-[t-butyldimethylsilyloxy)-5,5-dimethyl-6-hydroxymethylcyclohexene (16)

In a manner similiar to Scheme I, 15 (47.2 mmol) was treated with LAH (94.4 mmol) in THF and, after workup, and purification by HPLC using 8:1 hexanes:EtOAc as eluent provided 6.55 g of oily product.

D. 2-(4-Fluoro-3-methylphenyl)-4-(t-butyldimethylsilyloxy)-6,6-dimethylcyclohex-2-en-1-carboxaldehyde (17)

In a manner similiar to Scheme I, 16 (43.5 g, 0.115 mol) was treated with sulfur trioxide pyridine complex (56.0 g, 0.345 mol) in anhydrous DMSO and workup provided 21.6 g of brown oil which was taken forward without additional purification.

E. 2-(4-Fluoro-3-methylphenyl)-4-t-butyldimethylsilyloxy)-6,6-dimethylcyclohex-l-en-1-carboxaldehyde (18)

A solution of 17 (21.6 g, 57.4 mmol) and potassium t-butoxide (0.32 g, 2.87 mmol) in 250 mL anhydrous THF was stirred for 2 h and poured onto ether and dilute aqueous acetic acid. The organic layer was washed with $H_2O$, saturated $NaHCO_3$ and brine and dried ($MgSO_4$). Removal of the volatiles in vacuo provided 20.2 g of yellow oil which was taken forward without further purification.

F. (E)-3{(2-(4-fluoro-3-methylphenyl)-4-(t-butyldimethyl-silyloxy)-6,6-dimethylcyclohexen-1-yl)propenal (19)

In a manner similiar to Scheme I, 18 (20.2 g, 53.6 mmol) was treated with LDA-derived anion of ethylidenecyclohexylamine (12.8 g, 0.102 mol) and, after workup and purification by HPLC using 30:1 hexanes:EtOAc as eluent provided 13.5 g of an orange color oil.

G. Methyl (E)-7-(2-(4-fluoro-3-methylphenyl)-4-(t-butyldimethyl-silyloxy)-6,6-dimethylcyclohexen-1-yl}-5-hydroxy-3-oxohept-6-enoate In a manner similiar to Scheme I, 19 (13.45 g, 33.4 mmol) was treated with LDA-derived dianion of methyl acetoacetate (40.1 mmol) in THF and, after workup and purification by HPLC using 4:1 hexanes:EtOAc as eluent provided 7.8 g of an orange color oil.

H. Methyl (E)-7-(2-(4-fluoro-3-methylphenyl)-4-(t-butyldimethylsilyloxy)-6.6-dimethylcyclohexen-1-yl}-3,5-dihydroxyhept-6-enoate In a manner similiar to Scheme I, 20 (7.80 g, 15.1 mmol) was treated with triethylborane (22.6 mmol), NaBH$_4$ (17.3 mmol) and methanol (10 mL) in anhydrous THF at −78° C.. The workup provided 7.55 g of product as an oil which was taken forward without further purification.

I. Trans-(E)-6-(2-{2-(4-fluoro-3-methylphenyl)-4-(t-butyldimethylsilyloxy)-6,6-dimethylcyclohexen-1-yl)-ethenyl)-4-hydroxy-3,4,5,6-tetrahydro-2H-pyran-2-one (22)

In a manner similiar to Scheme I, 21 (7.55 g, 14.5 mmol) was treated with aqueous NaOH (14.5 mmol) in methanol at 0°-5° C. and after the usual workup provided 6.9 gm of acid. The acid (13.6 mmol) was treated with ethyl chloroformate (13.6 mmol) and triethylamine (13.6 mmol) in CH$_2$Cl$_2$. Purification by HPLC using 2:1 hexanes:EtOAc as eluent furnished 4.8 g of solid product.

J. Trans (E)-6-(2-(2-(4-fluoro-3-methylphenyl)-4-(t-butyldimethylsilyloxy)-6,6-dimethylcyclohexen-1-yl)-ethenyl)-4-t-butyldiphenylsilyloxy)-3.4,5.6-tetrahydro-2H-pyran-2-one (23)

To a solution of imidazole (1.84 g, 27.0 mmol) and tbutylchlorodiphenylsilane (3.71 g, 13.5 mmol) in 40 mL CH$_2$Cl$_2$ was added a solution of 22 (4.40 g, 9.0 mmol) in 40 mL of CH$_2$Cl$_2$. The reaction mixture was stirred overnight, diluted with ether, washed in H$_2$O and brine and dried (MgSO$_4$). Removal of the volatiles in vacuo provided a quantitative yield of the oily product.

K. Trans-(E)-6-(2-(2-(4-fluoro-3-methylphenyl)-4-hydroxy-6,6-dimethylcyclohexen-1-yl)ethenyl)-4-t-butyldiphenylsilyloxy)-3,4,5,6-tetrahydro-2H-ovran-2-one (24)

A solution of 23 (6.5 g) in 90 mL acetic acid, 30 mL THF and 30 mL H$_2$O was stirred overnight at ambient temperature and most of the volatiles were removed in vacuo. The residue was diluted with ether, washed with H$_2$O and brine and dried (MgSO$_4$). Removal of the volatiles in vacuo furnished a residue which was purified by HPLC using 2:1 hexanes:EtOAc as eluent. Concentration in vacuo of the product-rich fractions furnished 4.6 g of product.

EXAMPLE 3 (Scheme III)

A. Methyl 7-(4-fluorophenyl)-9.9-dimethyl-1,4-dioxaspiro-(4,5)-dec-6-en-8-carboxylate (25)

A solution of 4b (11,51 g, 41.7 mmol) 1,2-ethanediol (5.81 mL, 104 mmol) and PPTS (2.09 g, 8.34 mmol) in 100 mL toluene was heated with azeotropic removal of H$_2$O for 6 h, 1,2-ethanediol (2.9 mL) was added and heated overnight. The solution was cooled, diluted with ether, washed with saturated NaHCO$_3$, H$_2$O and brine and dried (MgSO$_4$). Removal of the volatiles in vacuo provided the oily product.

B. 7-(4-fluorophenyl)-9,9-dimethyl-1,4-dioxaspiro{4,5}-dec-7-en-8-carboxaldehyde (26)

To a solution of 25 (11.2 g, 35.0 mmol) in 100 mL of anhydrous THF at 0°-5° C. was added portionwise LAH (52.5 mmol). The mixture was stirred for 2 h and work-up provided 9.71 g of the oily alcohol. A mixture of the alcohol (97.1 g, 33.2 mmol), PCC (33.2 mmol) and celite (4 g) in 90 mL CH$_2$Cl$_2$ was stirred for 5 h at 0°-5° C., diluted with ether and filtered over SiO$_2$. Removal of the volatiles in vacuo and purification of the residue by HPLC using 14:1 hexanes:EtOAc as eluent provided 2.15 g of the oily product. To the aldehyde in 20 mL anhydrous THF was added potaspium t-butoxide (24 mg). The solution was stirred for 60 min and diluted with H$_2$O and ether. The organic layer was washed with H$_2$O and brine and dried (MgSO$_4$). Removal of the volatiles in vacuo provided 2.08 g of yellow solid which was taken forward without further purification

C. (E)-3-(7-(4-fluorophenyl)-9,9-dimethyl-1,4-dioxaspiro-{4,5}dec-7-en-8-yl)propenal (27)

In a manner similar to Scheme I, 26 (2.08 g, 7.17 mmol) was treated with the LDA-derived anion of ethylidenecyclohexylamine (1.36 g, 10.8 mmol) in anhydrous THF at 0°-5° C. and after workup and purification by SiO$_2$ using 6:1 hexanes:EtOAc as eluent provided 1.25 g of orange solid.

D. Methyl (E)-7-(7-(4-fluorophenyl)-9,9-dimethyl-1,4-dioxaspiro{4,5}dec-7-en-8-yl)-3,5-dihydroxyhept-6-enoate (28)

In a manner similar to Scheme I, 27 (1.25 g, 3.95 mmol) was treated with the dianion of methyl acetoacetate (3.76 mmol) in anhydrous THF at 0°-5° C. Workup and purification by SiO$_2$ using 2:1 hexanes:EtOAc as eluent gave 0.95 g of orange oil. The ketone was reduced with triethylborane, NaBH$_4$, and methanol in anhydrous THF at −78° C. Workup and purification by SiO$_2$ using 5:4 hexanes:EtOAc as eluent provided 0.80 g of the tan solid.

E. Trans-(E)-6-{2-{7-(4-fluorophenyl)-9,9-dimethyl-1,4-dioxaspiro{4,5}dec-7-en-8-yl}ethenyl}-4-hydroxy-3,4,5,6-tetrahydro-2H-pyran-2-one (29)

. A solution of 28 (0.80 g, 1.84 mmol) and NaOH (2.8 mL of a 1N aqueous solution) in 12 mL methanol was stirred for 2 h, cooled to 0°-5° C., acidified to pH 2 with aqueous HCl and extracted with ether. The combined organic extracts were washed with H$_2$O and brine and dried (MgSO$_4$). Removal of the volatiles in vacuo provided 0.60 g of yellow solid. A solution of the carboxylic acid, DCC (0.295 q, 1.43 mmol) and DMAP (9 mg, 0.071 mmol) in 10mL anhydrous ether was stirred for 1,5 h at −10° C. and placed on a SiO$_2$ gel column. Elution with 5:4 hexanes:EtOAc and concentration in vacuo of the product rich fractions furnished 0.38 g of white solid. mp 142°-4° C. Anal. C$_{32}$H$_{27}$FO$_5$. Theory C: 68.64; H: 6.76. Found C: 69.12; H: 6.97.

EXAMPLE 4 (Scheme IV)

A. Methyl 2-(4-fluoro-3-methylphenyl)-4-(pyrrolidin-1-yl)-6,6-dimethylcyclohex-2-en-1-carboxylate (31)

A solution of 4a (11.05 g, 38.1 mmol) and pyrrolidine (8.13 g, 0.114 mol) in 11,5 mL of 5N HCl in methanol (57.1 mmol) and 100 mL chloroform was stirred at ambient temperature overnight and the volatiles were removed in vacuo. The residue was dissolved in 100 mL methanol and 5N HCl methanol was added until the mixture became acidic (bromocresol green). To the solution was added NaCNBH$_3$ (2.40 g, 38.7 mmol) and the reaction was maintained at pH 3–5 by the dropwise addition of 5N HCl in methanol. After stirring overnight the volatiles were removed in vacuo. The residue was diluted with ether and 1N NaOH. The organic layer was washed with H$_2$O and brine and dried (MgSO$_4$). Removal of the volatiles in vacuo and purification of the residue by HPLC using 1% Et$_3$N in 1:1 hexanes:EtOAc as the eluent provided 8.75 g of the oily product.

B. 2-(4-Fluoro-3-methylphenyl)-4-(pyrrolidin-1-yl)-6,6-dimethylcyclohex-1-en-1-carboxaldehyde (32)

In a manner similar to Scheme I, 31 was treated sequentially with LAH in THF at 0°–5° C., sulfur trioxide pyridine complex in DMSO at ambient temperature and Triton B in methanol at 0°–5° C. for 18 h. Workup and purification afforded the oily product.

C. (E)-3-{2-(4-fluoro-3-methylphenyl)-4-(pyrrolidin-1-yl)-6,6-dimethylcyclohex-1-en-1-propenal (33)

In a manner similar to Scheme I, 32 (3.80 g, 12.1 mmol) was treated with the LDA-derived ahion of ethylidenecyclohexylamine (2.90 g, 23.2 mmol) in anhydrous ether. Workup and purification of the residue by HPLC using 1% Et$_3$N in 10:1 hexanes:EtOAc as eluent provided the dieneimine (2.4 g) The imine and oxalic acid (10 g) in 40 mL H$_2$O was heated at 100° C. for 2 h, cooled, diluted with saturated NaHCO$_3$ and ether. The organic layer was washed with H$_2$O and brine and dried (MgSO$_4$). Removal of volatiles in vacuo provided 2.27 g of gum which was taken forward without further purification.

D. Methyl (E)-7-{2-{2-(4-fluoro-3-methylphenyl)-4-(pyrrolidin-1-yl)-6,6-dimethylcyclohex-1-en-1-yl}-3,5-dihydroxyhept-6-enoate (34)

In a manner similar to Scheme I, 33 (2.27 g, 6,65 mmol) was treated with the LDA derived anion of methyl acetoacetate (7.98 mmol) followed by triethylborane, methanol, and NaBH$_4$. Workup and purification by HPLC using 1% Et$_3$N in EtOAc as eluent provided the oily product.

E. Trans-(E)-6-{2-{2-(4-fluoro-3-methylphenyl)-4-(pyrrolidin-1-yl)-6,6-dimethylcyclohex-1-en-1-yl}ethenyl)4-hydroxy-3,4,5,6-tetrahydro-2H-pyran-2-one (35)

In a manner similar to Scheme I, 34 (0.19 g) was treated with 2N NaOH in methanol at 0°–5° C. for 18 h, followed by ethyl chloroformate (0.254 mmol) and Et$_3$N in CH$_2$Cl$_2$ at 0°–5° C. Workup and purification of the residue by SiO$_2$ using 1% Et$_3$N in EtOAc as eluent yielded the product. mp 120°–3° C. Anal. C$_{26}$H$_{34}$FNO$_3$·0.5 H$_2$O: Theory C: 71,53; H: 8.08; N: 3.21; Found C: 71.60; H: 8.17; N: 3.03.

EXAMPLE 5 (Scheme V)

A. Trans-(E)-6-(2-{2-(4-fluoro-3-methylphenyl)-4-(ethoxycarbonylmethoxy)-6,6-dimethylcyclohexen-1-yl}ethenyl}-4-(t-butyldiuhenylsilyloxy)-3,4,5,6-tetrahydro-2H-pyran-2-one (36)

To a mixture of 24 (0.17 gm, 0.27 mmol) and Rh$_2$(OAc)$_4$ in 1,5 mL CH$_2$Cl$_2$ was added dropwise over 90 min. ethyl diazoacetate (200 μL, 1.93 mmol). The mixture was stirred for an additional 20 min. and the volatiles removed in vacuo. Purification of the residue on SiO$_2$ by eluting with 5:1 hexanes:EtOAc provided 0.12 gm of the oily product.

B. Trans-(E)-6-(2-(2-(4-fluoro-3-methylphenyl)-4-(ethoxycarbonylmethoxy)-6,6-dimethylcyclohexen-1-yl)-ethenyl)-4-hydroxy-3,4,5,6-tetrahydro-2H-pyran-2-one (37)

To a 0°–5° C. solution of 36 (0.11 gm) in 1 mL anhydrous THF was added 0.1 mL of acetic acid and 0.75 mL of a 1.1 M THF solution of tetrabutylammonium flouride. The solution was slowly warmed to 25° C., stirred overnight, diluted with ether, washed with saturated NaHCO$_3$ and brine and dried (MgSO$_4$). Removal of the volatiles in vacuo and purification of the residue on SiO$_2$ by eluting with 1:1 hexanes:EtOAc furnished the solid product.

EXAMPLE 6 (Scheme VI)

A. Trans-(E)-6-{2-{2-(4-flouro-3-methylphenyl)-4-phenylcarbamoyloxy-6,6-dimethylcyclohexen-1-yl}ethenyl}-4-(t-butyldiphenylsilyloxy)-3,4,5,6-tetrahydro-2H-pyran-2-one (38)

To a solution of 24 (0.258 g, 0.421 mmol) in 3 mL anhydrous DMF was added phenylisocyanate (52 μL, 0.463 mmol). The mixture was stirred for 4 h, and phenylisocyanate (52 μL) was added again. The reaction was stirred overnight, diluted with ether, washed with H$_2$O and brine and dried (MgSO$_4$). Removal of the volatiles in vacuo and purification of the residue with SiO$_2$ using 3:1 hexanes:EtOAc as eluents provided 0.210 gm of the white solid.

B. Trans-(E)-6-(2-(2-(4-flouro-3-methylphenyl)-4-phenylcarbamoyloxy-6,6-dimethylcyclohexen-1-yl}ethenyl}-4-hydroxy-3,4,5,6-tetrahydro-2H-pyran-2-one (39)

In a manner similar to Scheme V, 38 (0.20 gm) was treated with tetrabutylammonium fluoride in THF and acetic acid and, after workup, purified by SiO$_2$ using 1:1 hexanes:EtOAc as eluent and yielded 0.101 g of product. mp 73°–5° C. Anal. C$_{29}$H$_{32}$FNO$_5$: Theory C: 70.57; H: 6.54; N:2.84. Found C: 70.37; H: 6.94; N: 3.06.

EXAMPLE 7 (Scheme VII)

A.
Trans-(E)-6-{2-(2-(4-fluoro-3-methylphenyl)-4-ethyl-carbonyldioxy-6,6-dimethylcyclohex-1-en-1-yl}ethenyl}-4-butyldiphenylsilyloxy)-3,4,5,6-tetrahydro-2H-pyran-2one (40)

A solution of 24 (0.25 g, 0.408 mmol) and freshly distilled ethyl chloroformate (81 μL, 0.816 mmol) in 3 mL anhydrous pyridine was heated at 60° C. for 5 h, cooled, diluted with ether, washed with H$_2$O, aqueous HCl and brine and dried (MgSO$_4$). Removal of the volatiles in vacuo provided a residue which was purified by flash chromatography using 6:1 hexanes—EtOAc as the eluent. Concentration in vacuo of the product rich fractions provided 0.15 g of the off-white solid.

B.
Trans-(E)-6-(2-(2-(4-fluoro-3-methylphenyl)-4-ethyl-carbonyldioxy-6,6-dimethylcyclohex-1-en-1-yl}ethenyl}-4-hydroxy-3,4,5,6-tetrahydro-2H-pyran-2-one (41)

In a manner similar to Scheme V, 40 (0.15 g, 0.219 mmol) was treated with n-tetrabutylammonium fluoride (1.1 mmol) in THF. Workup and purification by HPLC using 1:1 hexanes:EtOAc as eluent yielded 70 mg of product. Anal. C$_{25}$H$_{31}$FO$_6$: Theory C: 67.25; H: 7.00. Found C: 66.83; H:71.00.

EXAMPLE 8 (Scheme VIII)

A.
Trans-(E)-6-{2-{2-(4-fluoro-3-methylphenyl)-4-succinimido-6,6-dimethylcyclohexen-1-yl}ethenyl}-4-(t-butyldiphenylsilyloxy)-3,4,5,6-tetrahydro-2H-pyran-2-one (42)

To a solution of 24 (0.324 g, 0.52 mmol), succinimide (57.6 mg, 0.58 mmol) and triphenylphosphine (0.153 gm, 0.58 mmol) in 3 mL anhydrous THF was added dropwise diethyl azodicarboxylate (92 μL, 0.58 mmol). The mixture was stirred for 3 h and the volatiles removed in vacuo. Purification of the residue on SiO$_2$ by eluting with 1:1 hexanes:EtOAc provided 0.13 gm of the oily product.

B.
Trans-(E)-6-{2-{2-(4-fluoro-3-methylphenyl)-4-succinimido-6,6-dimethylcyclohexen-1-yl}ethenyl}-4-hydroxy-4,5,6-tetrahydro-2H-pyran-2-one (43)

In a manner similar to scheme V, 42 (0.13 gm) was treated with tetrabutylammonium fluoride and the product was purified by SiO$_2$ with 1,5:1 EtOAc:hexanes is the eluent. Concentration in vacuo of the product rich fractions provided 0.51 gm of the product. mp 71°–77° C. Anal. C$_{26}$H$_{30}$FNO$_5$.0.25 H$_2$O: Theory C: 67.89; H: 6.68; N: 3.04. Found C: 67.83; H: 6.95; N: 2.90.

EXAMPLE 9 (Scheme IX)

A.
Trans-(E)-6-{2-{2-(4-fluoro-3-methylphenyl)-4-phthalimido-6,6-dimethylcyclohexen-1-yl)ethenyl}-4-(t-butyldiphenylsilyloxy)-3,4,5,6-tetrahydro-2H-pyran-2-one (44)

In a manner similar to Scheme VIII, 24 (0.242 gm), triphenylphosphine, (0.114 g), phthalimide (64 mg) and diethyl azodicarboxylate (68 μL) provided, after SiO$_2$ chromatography with 5:1 hexanes:EtOAc as eluent, 0.16 gm of the oily product.

Trans-(E)-6-{2-{2-(4-fluoro-3-methylphenyl)-4-phthalimido-6,6-dimethylcyclohexen-1-yl}ethenyl}-4-hydroxy-3,4,5,6-tetrahydro-2H-pyran-2-one (45)

In a manner similar to Scheme VIII, 44 (0.15 gm) was treated with tetrabutylammonium fluoride and HOAc and provided, after purification with SiO$_2$ using 1:1 hexanes:EtOAc as eluent, 68 mg of the solid product.

In manner similar to the processes shown in the above Examples, the following compounds are made:

Trans-(E)-6-[2-[8-(4-fluoro-3-methylphenyl)-3,3,10,10-tetramethyl-1,5-dithiaspiro[5.5]undec-8-en-9-yl]ethenyl]-4-hydroxy-3,4,5,6-tetrahydro-2H-pyran-2-one. 1,5-dioxospiro[5.5]undec-8-en-9-yl]ethenyl]-4-hydroxy-3,4,5,6-tetrahydro-2H-pyran-2-one.

Trans-(E)-6-[2-[8-(4-fluorophenyl)-2,3,9,9-tetramethyl-1,4-dithiaspiro[4.5]dec-7-en-8-yl]ethenyl]-4-hydroxy-3,4,5,6-tetrahydro-2H-pyran-2-one.

Trans-(E)-6-[2-[-2-(4-fluoro-3-methylphenyl)-4-(3,4-difluorophenylcarbonyldioxy)-6,6-dimethylcyclohex-1-en-1yl]ethenyl]-4-hydroxy-3,4,5,6-tetrahydro-2H-pyran-2-one.

Trans-(E)-6-[2-[2-(4-fluoro-3-methylphenyl)-4-(4-pyridylcarbonylhydroxy)-6,6-dimethylcyclohex-1-en-1yl]ethenyl]-4-hydroxy-3,4,5,6-tetrahydro-2H-pyran-2-one.

Trans-E-(6-[2-[2-(4-fluoro-3-methylphenyl)-4-ethylcarbamoyloxy-6,6-dimethylcyclohex-1-en-1-yl]ethenyl]-4-hydroxy-3,4,5,6-tetrahyro-2H-pyran-2-one.

Trans-6-[2-[2-(4-chloro-3-methylphenyl)-4-(4-chloro-3-methylphenylcarbamoyloxy)-6,6-dimethylcyclohex-1-en-1yl]ethyl]-4-hydroxy-3,4,5,6-tetrahydro-2H-pyran-2-one.

Trans-6-[2-[2-(4-fluorophenyl)-4-(3-pyridyl-carbamoyloxy)-6,6-dimethyloyclohex-1-en-1-yl]-ethyl]4-hydroxy-3,4,5,6-tetrahydro-2H-pyran-2-one.

Trans-6-[2-[2-(4-flouorphenyl)-4-(5-indolylcarbamoyloxy)-6,6-dimethylcyclohex-1-en-1-yl]ethenyl]-4hydroxy-3,4,5,6-tetrahydro-2H-pyran-2-one.

Trans-6-[2-[2-(4-fluorophenyl)-4-(3-quinolinylcarbamoyloxy)-6,6-dimethylcyclohex-1-en-1-yl]ethyl]-4-hydroxy-3,4,5,6-tetrahydro-2H-pyran-2-one.

Trans-6-[2-[2-(4-flouro-3-methylphenyl)-4-(3-quinolinylcarbonyldioxy)-6,6-dimethylcyclohex-1-en-1yl]ethyl]-4-hydroxy-3,4,5,6-tetrahydro-2H-pyran-2-one.

Trans-(E)-6-[2-[2-(4-fluoro-3-hydroxymethyl)-4-(3-(diethylaminocarbonyl)propyloxy)-6,6-dimethylcyclohex-1-en-1-yl]ethenyl]-4-hydroxy-3,4,5,6-tetrahydro-2H-pyran-2-one.

Trans-(E)-6-[2-[2-(4-fluoro-3-methylphenyl)-4-(3-(ethoxycarbonyl)propyloxy)-6,6-dimethylcyclohex-1-en-1yl]ethenyl]-4-hydroxy-3,4,5,6-tetrahydro-2H-pyran-2-one.

Trans-(E)-6-[2-[2-(4-fluoro-3-methylphenyl)-4-(3-(4-fluoro-3-methylbenzoyl)propyloxy)-6,6-dimethylcyclohex-1-en-1yl]ethenyl]-4-hydroxy-3,4,5,6-tetrahydro-2H-pyran-2-one.

Trans-(E)-6-[2-[2-(4-fluorophenyl)-4-(3-(2,6-dimethyl-4-pyridoyl)propyloxy)-6,6-dimethyl-cyclohex-1-en-1yl]ethenyl]-4-hydroxy-3,4,5,6-tetrahydro-2H-pyran-2-one.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test method described hereunder. The method is based on the articles: "Purification of 3-hydroxy-3-methylglutaryl-coenzyme A reductase from rat liver" by Kleinsek et al., Proc. Natl. Acad. Sci. USA, Vol. No. 4, pp. 1431-1435, Apr. 1977 Biochemistry; "Mevinolin: A highly potent competitive inhibitor of hydroxy methyl glutaryl-coenzyme A reductase and a cholesterol-lowering agent" by Alberts et al., Proc. Natl. Acad. Sci. U.S.A., Vol 77, pp. 3951-3961, July 1980, Biochemistry; "Effects of ML-236B on cholesterol metabolism in mice rats: Lack of hypocholesterolemic activity in normal animals" by Endo et et al., Biochimica et Biophysica Acta, 575 (1979) 266-276; and "Evidence of regulation of 3-hydroxy-3-methylglutaryl coenzyme A reductase activity and cholesterol synthesis in nonhepatic tissues of rat" by Balasubramaniam et al., Proc. Natl. Acad. Sci. USA, Vol. 73, No. 8, pp. 2564-2568, Aug. 1976, Biochemistry.

The method used (designated HMGR Screen) was as follows. Male rats were acclimated to an alternate 12 hour light-dark cycle for a period of 2-3 weeks. The animals, weighing 180-230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at $-80°$ C. in 300 $\mu$l portion samples. Prior to use, the enzyme was activated at 37° C. for 30 minutes in a reaction mixture. The reaction mixture contained in a volume of 240 $\mu$l: 0.14M potassium phosphate buffer (pH 7.0); 0.18M KCl; 3,5 mM EDTA; 10 mM dithiothreitol; 0.1 mg/ml BSA; 30,000 cpm of [$^{14}$C]HMG-CoA; $\mu$M HMG-CoA, and 200 $\mu$g of solubilized enzyme with and without inhibitors (in 10 $\mu$l DMSO). After 5 minutes incubation at 37° C. the reaction was initiated with 0.2 mM NADPH. The final assay volume was 300 $\mu$l. The reaction then was terminated with 100 $\mu$l of 1N HCl. After an additional incubation for 15 minutes at 37° C. to allow for complete lactonization of the product, the mixture was diluted with 3 ml GDW. The diluted mixture was then poured over a 0.7×1.4 cm column containing 100-200 mesh Bio-Rex ion-exchange resin (cloride form of Bio-Rad) which was equilibrated with distilled water. With this resin the unreacted [$^{14}$C] HMG-CoA was adsorbed and the product [$^{14}$C] lactone was eluted (80% recovery) directly into scintillation vials. After the addition of 10 ml of Aquasol, radioactivities of the samples were measured in a scintillation counter. Result on compounds 13, 29, 35, 37, 139, 41, 43 and 45 are shown in Table I (IC$_{50}\mu$M).

TABLE I

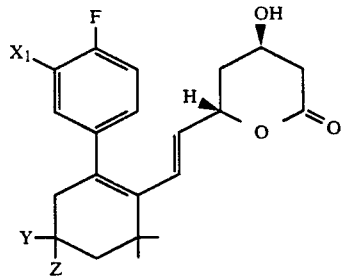

| Compound | X$_1$ | Z | Y | IC$_{50}$ ($\mu$M) |
|---|---|---|---|---|
| 13 | Me | Chemical bond | —S(CH$_2$)$_3$S— | 0.011 |
| 29 | H | Chemical bond | —O(CH$_2$)$_2$O— | 0.038 |
| 35 | Me | H | C$_4$H$_8$N— | >0.100 |
| 37 | Me | H | EtOC(O)CH$_2$O— | 0.030 |
| 39 | Me | H | PhNHC(O)— | 0.0018 |
| 41 | Me | H | EtOC(O)O— | 0.042 |
| 43 | Me | H | N-Succinimido | 0.0080 |
| 45 | Me | H | N-Phthalimido | 0.100 |

What is claimed is:
1. A compound of the formula

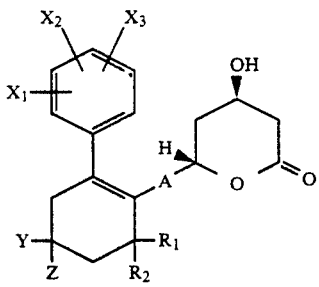

wherein
A is CH₂CH₂, CH=CH, or C≡C;
X₁, X₂ and X₃ are independently: H, C₁₋₆ alkyl, halogen, RO(CH₂)$_m$—, aryl, NR₁R₂ or SO$_m$R₁;
R, R₁, R₂ and Z are independently: H or C₁₋₆ alkyl;
Y is

Q is NR₃R₄ or OR₃;
R₃ and R₄ are independently: H, C₁₋₆ alkyl, aryl, substituted aryl, heteroaryl, or substituted heteroaryl selected from the group consisting of pyridyl, indolyl, quinolyl, substituted pyridyl, substituted indolyl and substituted quinolyl;
m is 0, 1 or 2;
or a hydroxy acid or pharmaceutically acceptable salt thereof.

2. A hypocholesterolemic, hypolipidemic pharmaceutical composition comprising a therapeutically effective amount of a compound of claim 1 and a pharmaceutically acceptable carrier.

3. A hypocholesterolemic, hypolipidemic pharmaceutical composition of claim 2 wherein said compound is selected from the group consisting of:
trans-(E)-6-{2-{2-(4-fluoro-3-methylphenyl)-4-phenylcarbamoyloxy-6,6-dimethyclohex-1-en-1-yl)ethenyl)-4-hydroxy-3,4,5,6-tetrahydro-2H-pyran-2-one;
trans-(E)-6-{2-{2-(4-fluoro-3-hydroxymethyl)-4-(4-fluorophenylcarbamoyloxy)-6,6-dimethyclohex-1-en-1-yl}ethenyl}-4-hydroxy-3,4,5,6-tetrahydro-2H-pyran-2-one;
trans-6-{2-{2-(4-fluorophenyl)-4-(N-phenyl-N-methylcarbamoyloxy)-6,6-dimethylclohex-1-en-1-yl)ethyl)-4-hydroxy-3,4,5,6-tetrahydro-2H-pyran-2-one;
trans-(E)-6-{2-{2-(4-chlorophenyl)-4-(3-(pyridylcarbamoyloxy)-6,6-dimethyclohex-1-en-1-yl}ethenyl}-4-hydroxy-3,4,5,6-tetrahydro-2H-pyran-2-one;
trans-(E)-6-{2-{2-(4-fluorophenyl)-4-ethylcarbonyldioxy)-6,6-dimethyclohex-1-en-1-yl}ethyl}-4-hydroxy-3,4,5,6-tetrahydro-2H-pyran-2-one.

4. A hypocholesterolemic, hypolipidemic pharmaceutical composition of claim 2 wherein said compound is selected from the group consisting of:
trans-(E)-6-{2-{2-(4-chloro-3-methylphenyl)-4-(4-chloro-3-methylphenylcarbonyldioxy)-6,6-dimethylcyclohex-1-en-1yl}ethenyl}-4-hydroxy-3,4,5,6-tetrahydro-2H-pyran-2-one;
trans-(E)-6-[2-[-2-(4-fluoro-3-methylphenyl)-4-(3,4-difluorophenylcarbonyldioxy)-6,6-dimethylcyclohex-1-en-1-yl]ethenyl]-4-hydroxy-3,4,5,6-tetrahydro-2H-pyran-2-one;
trans-(E)-6-[2-[2-(4-fluoro-3-methylphenyl)-4-(4-pyridylcarbonyldioxy)-6,6-dimethylcyclohex-1-en-1-yl]ethenyl]-4-hydroxy-3,4,5,6-tetrahydro-2H-pyran-2-one; and
trans-E-(6-[2-[2-(4-fluoro-3-methylphenyl)-4-ethylcarbamoyloxy-6,6-dimethylcyclohex-1-en-1-yl]ethenyl]-4-hydroxy-3,4,5,6-tetrahyro-2H-pyran-2-one.

5. Trans-6-[2-[2-(4-chloro-3-methylphenyl)-4-(4-chloro-3-methylphenylcarbamoyloxy)-6,6-dimethylcyclohex-1-en-1yl]ethyl]-4-hydroxy-3,4,5,6-tetrahydro-2H-pyran-2-one.

6. Trans-6-[2-[2-(4-fluorophenyl)-4-(3-pyridylcarbamoyloxy)-6,6-dimethyloyclohex-1-en-1-yl]-ethyl]4-hydroxy-3,4,5,6,-tetrahydro-2H-pyran-2-one.

7. Trans-6-[2-[2-(4-flouorphenyl)-4-(5-indolylcarbamoyloxy)-6,6-dimethylcyclohex-1-en-1-yl]ethyl]4hydroxy-3,4,5,6-tetrahydro-2H-pyran-2-one.

8. Trans-6-[2-[2-(4-fluorophenyl)-4-(3-quinolinylcarbamoyloxy)-6,6-dimethylcyclohex-1-en-1-yl]-ethyl]-4-hydroxy-3,4,5,6-tetrahydro-2H-pyran-2-one.

9. Trans-6-[2-[2-(4-flouro-3-methylphenyl)-4-(3-quinolinylcarbonyldioxy)-6,6-dimethylcyclohex-1-en-1yl]ethyl]-4-hydroxy-3,4,5,6-tetrahydro-2H-pyran-2-one.

10. A hypocholesterolemic, hypolipidemic pharmaceutical composition of claim 1 wherein said compound is selected from the group consisting of:
trans-6-[2-[2-(4-chloro-3-methylphenyl)-4-(4-chloro-3-methylphenylcarbamoyloxy)-6,6-dimethylcyclohex-1-en-1-yl]ethyl]-4-hydroxy-3,4,5,6-tetrahydro-2H-pyran-2-one;
trans-6-[2-[2-(4-fluorophenyl)-4-(3-pyridyl-carbamoyloxy)6,6-dimethyloyclohex-1-en-1-yl]-ethyl]4-hydroxy-3,4,5,6,-tetrahydro-2H-pyran-2-one; trans-6-[2-[2-(4-flouorphenyl)-4-(5-indolyl-cabamoyloxy)-6,6-dimethylcyclohex-1-en-1-yl]ethyl]-4hydroxy-3,4,5,6-tetrahydro-2H-pyran-2-one.

11. A hypocholesterolemic, hypolipidemic pharmaceutical composition of claim 1 wherein said compound is selected from the group consisting of:
trans-6-[2-[2-(4-fluorophenyl)-4-(3-quinolinylcarbamoyloxy)6,6-dimethylcyclohex-1-en-1-yl]-ethyl]-ethyl]-4-hydroxy-3,4,5,6-tetrahydro-2H-pyran-2-one;
trans-6-[2-[2-(4-flouro-3-methylphenyl)-4-(3-quinolinylcarbonyldioxy)-6,6-dimethylcyclohex-1-en-1-yl]ethyl]-4-hydroxy-3,4,5,6-tetrahydro-2H-pyran-2-one.

12. A method of inhibiting cholesterol synthesis in a patient in need of such treatment comprising administering a pharmaceutical comopsition defined in claim 2.

13. A compound of the formula

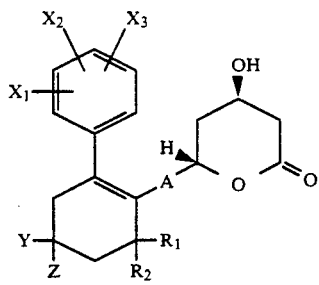

wherein

A is CH$_2$CH$_2$, CH=CH, or C≡C;

X$_1$, X$_2$ and X$_3$ are independently: H, C$_{1-6}$ alkyl, halogen, RO(CH$_2$)$_m$—, aryl, NR$_1$R$_2$ or SO$_m$R$_1$;

R, R$_1$, R$_2$ and Z are independently: H or C$_{1-6}$alkyl;

Y is —O(CR$_1$R$_2$)$_n$C(O)Q;

Q is NR$_3$R$_4$ or OR$_3$;

R$_3$ and R$_4$ are independently: H, C$_{1-6}$alkyl, aryl, substituted aryl, heteroaryl or substituted heteroaryl selected from the group consisting of pyridyl, indolyl, quinolyl, substitutedpyridyl, substituted indolyl and substituted quinolyl;

n is 1, 2 or 3;

m is 0, 1 or 2;

or a hydroxy acid or pharmaceutically acceptable salt thereof.

14. Trans-(E)-6-[2-[2-(4-fluoro-3-methylphenyl)-4-phenylcarbonyloxy-6,6-dimethyloxycyclohexen-1-yl]ethenyl]-4-hydroxy-3,4,5,6-tetrahydro-2H-pyran-2-one.

15. Trans-(E)-6-[2-[2-(4-fluoro-3-methylphenyl)-4-ethylcarbonyldioxy-6,6-dimethyloxycyclohex-1-en-1-yl]ethenyl]-4-hydroxy-3,4,5,6-tetrahydro-2H-pyran-2-one.

16. Trans-(E)-6-[2-[2-(4-fluorophenyl)-4-(3-(2,6-dimethyl-4-pyridoyl)propyloxy)-6,6-dimethyl-cyclohex-1-en-1yl]ethenyl]-4-hydroxy-3,4,5,6-tetrahydro-2H-pyran-2-one.

17. A hypocholesterolemic, hypolipidemic pharmaceutical composition comprising a therapeutically effective amount of a compound of claim 13 and a pharmaceutically acceptable carrier.

18. A hypocholesterolemic, hypolipidemic pharmaceutical composition of claim 17 wherein said compound is selected from the group consisting of:

trans-6-[2-[2-(4-fluoro-3-methylphenyl)-4-ethoxycarbonylmethoxy)-6,6-dimethylcyclohex-1-en-1-yl]ethyl]-4-hydroxy-3,4,5,6-tetrahydro-2H-pyran-2-one;

trans-(E)-6-[2-[2-(4-fluorophenyl)-4-(2-[ethoxycarbonyl)-ethoxy)-6,6-dimethylcyclohex-1-en-1-yl]ethenyl]-4-hydroxy3,4,5,6-tetrahydro-2H-pyran-2-one;

trans-(E)-6-[2-[2-(4-fluoro-3-ethylphenyl)-4-(2-(4-fluoroanilinocarbonyl)ethoxy)-6,6-dimethylcyclohex-1-en-1-yl[ethenyl]-4-hydroxy-3,4,5,6-tetrahydro-2H-pyran-2-one;

trans-(E)-6-[[2-(4-chlorophenyl)-4-(dimethylaminocarbonylmethoxy)-6,6-dimethylcyclohex-1-en-1-yl]ethynyl]-4-hydroxy-3,4,5,6-tetrahydro-2H-pyran-2-one; and trans-(E)-6-[2-[2-(4-fluoro-3-methylphenyl)-4-(4-methoxyanilinocarbonylmethoxy)-6,6-dimethylcyclohex-1-en-1-yl]ethyl]-4-hydroxy-3,4,5,6-tetrahydro-2H-pyran-2-one.

19. A hypocholesterolemic, hypolipidemic pharmaceutical composition of claim 17 wherein said compound is selected from the group consisting of:

trans-(E)-6-[2-[2-(4-fluoro-3-hydroxymethyl)-4-(3-(diethylaminocarbonyl)propyloxy)-6,6-dimethyl-cyclohex-1-en-1-yl]-ethenyl]-4-hydroxy-3,4,5,6-tetrahydro-2H-pyran-2-one;

trans-(E)-6-[2-[2-(4-fluoro-3-methylphenyl)-4-(3-(ethoxycarbonyl)propyloxy)-6,6-dimethylcyclohex-1-en-1-yl]-ethenyl]-4-hydroxy-3,4,5,6-tetrahydro-2H-pyran-2-one; and trans-(E)-6-[2-[2-(4-fluoro-3-methylphenyl)-4-(3-(4-fluoro3-methylbenzoyl)propyloxy)-6,6-dimethyl-cyclohex-1-en-1yl]ethenyl]-4-hydroxy-3,4,5,6-tetrahydro-2H-pyran-2-one; trans-(E)-6-[2-[2-(4-fluorophenyl)-4-(3-(2,6-dimethyl-4-pyridoyl)-propyloxy)-6,6-dimethyl-cyclohex-1-en-1yl]ethenyl]-4-hydroxy-3,4,5,6-tetrahydro-2H-pyran-2-one.

20. A method of inhibiting cholesterol synthesis in a patient in need of such treatment comprising administering a pharmaceutical composition defined in claim 17.

* * * * *